United States Patent
Meier et al.

(10) Patent No.: US 12,016,328 B2
(45) Date of Patent: Jun. 25, 2024

(54) PH ADJUSTMENT TO IMPROVE THAW RECOVERY OF CELL BANKS

(71) Applicant: Genentech, Inc., South San Francisco, CA (US)

(72) Inventors: Angela Meier, San Francisco, CA (US); Steven J. Meier, Burlingame, CA (US); Phillip Duffy, Brisbane, CA (US); Marcia Coyne, San Mateo, CA (US); Kara Calhoun, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 132 days.

(21) Appl. No.: 17/497,330

(22) Filed: Oct. 8, 2021

(65) Prior Publication Data

US 2022/0151221 A1    May 19, 2022

Related U.S. Application Data

(60) Division of application No. 16/798,014, filed on Feb. 21, 2020, now abandoned, which is a division of application No. 15/399,666, filed on Jan. 5, 2017, now Pat. No. 10,602,739, which is a continuation of application No. PCT/US2015/039757, filed on Jul. 9, 2015.

(60) Provisional application No. 62/022,392, filed on Jul. 9, 2014.

(51) Int. Cl.
| | | |
|---|---|---|
| *A01N 1/02* | (2006.01) | |
| *C12N 5/00* | (2006.01) | |
| *C12N 5/071* | (2010.01) | |
| *C12N 5/10* | (2006.01) | |
| *C12N 15/16* | (2006.01) | |

(52) U.S. Cl.
CPC ......... *A01N 1/0221* (2013.01); *A01N 1/0284* (2013.01); *C12N 5/0018* (2013.01); *C12N 5/0682* (2013.01); *C12N 2510/02* (2013.01)

(58) Field of Classification Search
None
See application file for complete search history.

(56) References Cited

U.S. PATENT DOCUMENTS

| | | |
|---|---|---|
| RE30,985 E | 6/1982 | Cartaya |
| 4,515,893 A | 5/1985 | Kung |
| 4,560,655 A | 12/1985 | Baker |
| 4,657,866 A | 4/1987 | Kumar |
| 4,767,704 A | 8/1988 | Cleveland |
| 4,816,567 A | 3/1989 | Cabilly |
| 4,927,762 A | 5/1990 | Darfler |
| 5,091,313 A | 2/1992 | Chang |
| 5,122,469 A | 6/1992 | Mather |
| 5,545,806 A | 8/1996 | Lonberg |
| 5,545,807 A | 8/1996 | Surani |
| 5,569,825 A | 10/1996 | Lonberg |
| 5,622,700 A | 4/1997 | Jardieu |
| 5,625,126 A | 4/1997 | Lonberg |
| 5,633,425 A | 5/1997 | Lonberg |
| 5,661,016 A | 8/1997 | Lonberg |
| 5,672,347 A | 9/1997 | Aggarwal |
| 5,693,762 A | 12/1997 | Queen |
| 5,714,338 A | 2/1998 | Wai Fei et al. |
| 5,721,108 A | 2/1998 | Robinson |
| 5,725,856 A | 3/1998 | Hudziak |
| 5,736,137 A | 4/1998 | Anderson |
| 10,602,739 B2 | 3/2020 | Meier |
| 2003/0049840 A1 | 3/2003 | Demetriou |
| 2006/0257842 A1 | 11/2006 | Pettegrew |
| 2009/0029340 A1 | 1/2009 | Gabbai |
| 2009/0142830 A1 | 6/2009 | Yamashiro et al. |
| 2009/0197331 A1 | 8/2009 | Kato |
| 2010/0261640 A1* | 10/2010 | Branco ............ A61P 31/14 435/5 |
| 2017/0112122 A1 | 4/2017 | Meier |
| 2020/0315162 A1 | 10/2020 | Meier et al. |

FOREIGN PATENT DOCUMENTS

| | | |
|---|---|---|
| EP | 0420937 B1 | 11/1994 |
| EP | 1257168 B1 | 2/2005 |
| EP | 2721930 A1 | 4/2014 |
| JP | H06046840 A | 2/1994 |
| JP | 2007252245 A | 10/2007 |
| RU | 2508397 C1 | 2/2014 |
| WO | 1987000195 A1 | 1/1987 |
| WO | 1990003430 A1 | 4/1990 |
| WO | 1991010741 A1 | 7/1991 |
| WO | 199304173 A1 | 3/1993 |
| WO | 199314191 A1 | 7/1993 |
| WO | 199519181 A1 | 7/1995 |
| WO | 199523865 A1 | 9/1995 |

(Continued)

OTHER PUBLICATIONS

Sigma Aldrich, Cryopreservation of Cell Lines, 2013, publication, pp. 1-10.*

(Continued)

*Primary Examiner* — Maria Marvich
(74) *Attorney, Agent, or Firm* — MORRISON & FOERSTER LLP

(57) ABSTRACT

Provided herein are methods of freezing mammalian cells for storage or improving thaw recovery of cell banks comprising freezing mammalian cells in a freezing medium having a pH of 6.7 to 8.5.

8 Claims, 6 Drawing Sheets

(56) References Cited

FOREIGN PATENT DOCUMENTS

| WO | 199630046 A1 | 10/1996 |
| WO | 1996033735 A1 | 10/1996 |
| WO | 1996034096 A1 | 10/1996 |
| WO | 199640210 A1 | 12/1996 |
| WO | 199726912 A2 | 7/1997 |
| WO | 199806248 A2 | 2/1998 |
| WO | 199823761 A1 | 6/1998 |
| WO | 199824893 A2 | 6/1998 |
| WO | 199845331 A2 | 10/1998 |
| WO | 199851793 A1 | 11/1998 |
| WO | 199901556 A2 | 1/1999 |
| WO | 200019817 A1 | 4/2000 |
| WO | 200075348 A1 | 12/2000 |
| WO | 200123592 A2 | 4/2001 |
| WO | 200137655 A1 | 5/2001 |
| WO | 200140309 A2 | 6/2001 |
| WO | 200123592 A3 | 12/2001 |
| WO | 2005094576 A2 | 10/2005 |
| WO | 2007077560 A2 | 7/2007 |
| WO | 2011047380 A2 | 4/2011 |
| WO | WO 2011089391 | * 7/2011 |
| WO | 2012028967 A2 | 3/2012 |
| WO | 2014160000 A1 | 10/2014 |
| WO | WO 2015150394 | * 10/2015 |

OTHER PUBLICATIONS

Kleman et al., Optimal Conditions for Freezing CHO-S and HEK293-EBNA Cell Lines: Influence of Me2SO, Freeze Density, and PEI-Mediated Transfection on Revitalization and Growth of Cells, and Expression, Biotechnology and Bioengineering, vol. 100, No. 5, Aug. 1, 2008, pp. 911-922.*

Barnes, D. et al. (Mar. 1, 1980). "Methods for Growth of Cultured Cells in Serum-Free Medium," Anal. Biochem. 102(2):255-270.

Brüggemann, M. et al. (1993). "Designer Mice: The Production of Human Antibody Repertoires in Transgenic Animals," Year in Immuno. 7:33-40.

Carter, P. et al. (May 1992). "Humanization of an Anti-p185HER2 Antibody for Human Cancer Therapy," Proc. Natl. Acad. Sci. USA 89:4285-4289.

Ceriani, R.L. et al. (Dec. 1, 1995). "Biological Activity of Two Humanized Antibodies Against Two Different Breast Cancer Antigens and Comparison to Their Original Murine Forms," Cancer Res. 55(23):5852s-5856s.

Choy. E.H.S. et al. (Jan. 1996). "Percentage of Anti-CD4 Monoclonal Antibody-Coated Lymphocytes in the Rheumatoid Joint is Associated With Clinical Improvement," Arthritis Rheum 39(1):52-56.

Clackson, T. et al. (Aug. 15, 1991). "Making Antibody Fragments Using Phage Display Libraries," Nature 352:624-628.

Dhainaut, J.-F. A. et al. (1995). "CDP571, A humanized Antibody to Human Tumor Necrosis Factor-α: Safety, Pharmacokinetics, Immune Response, and Influence of the Antibody on Cytokine Concentrations in Patients With Septic Shock," Crit. Care Med. 23(9):1461-1469.

Ellis, J.H. et al. (1995). "Engineered Anti-CD38 Monoclonal Antibodies for Immunotherapy of Multiple Myeloma," J. Immunol. 155(2):925-937.

Fellouse, F.A. et al. (Aug. 24, 2004). "Synthetic Antibodies From a Four-Amino-Acid Code: A Dominant Role for Tyrosine in Antigen Recognition," Proc. Natl. Acad. Sci. USA 101(34):12467-12472.

Fishwild, D.M. et al. (Jul. 1996). "High-avidity human IgGK Monoclonal Antibodies from a Novel Strain of Minilocus Transgenic Mice," Nature Biotechnol. 14:845-851.

Graham. F.L. et al. (1977). "Characteristics of a Human Cell Line Transformed by DNA from Human Adenovirus Type 5," J. Gen Virol. 36:59-74.

Graziano, R.F. et al. (1995). "Construction and Characterization of a Humanized Anti-γ-Ig Receptor Type I (FcγRI) Monoclonal Antibody," J. Immunol. 155(10):4996-5002.

Ham, R.J. et al. (1979). "Media and Growth Requirements," Meth. Enz. 58:44-93.

Hammerling, G.J. et al. (1981). "Production of Antibody-Producing Hybridomas in the Rodent Systems," in Research Monographs in Immunology, Elsevier/North-Holland Biomedical Press 3:563-587.

Hongo, J.A.S. et al. (1995). "Development and Characterization of Murine Monoclonal Antibodies to the Latency-Associated Peptide of Transforming Growth Factor β1," Hybridoma 14(3):253-260.

Hourmant, M. et al. (Aug. 1994). "Administration of An Anti-CD11a Monoclonal Antibody in Recipients of Kidney Transplantation: A Pilot Study," Transplantation 58:377-380.

Jakobovits, A. et al. (Mar. 18, 1993). "Germ-Line Transmission and Expression of a Human-Derived Yeast Artificial Chromosome," Nature 362:255-258.

Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90(6):2551-2555.

Jurcic, J.G. et al. (Dec. 1, 1995). "Radiolabeled Anti-CD33 Monoclonal Antibody M195 for Myeloid Leukemias," Cancer Res. 55(23 Suppl):5908s-5910s.

Juweid, M. et al. (Dec. 1, 1995). "Treatment of Non-Hodgkin's Lymphoma with Radiolabeled Murine, Chimeric, or Humanized LL2, and Anti-CD22 Monoclonal Antibody," Cancer Res 55(23 Suppl):5899s-5907s.

Kim, K.J. et al. (1992). "The Vascular Endothelial Growth Factor Proteins: Identification of Biologically Relevant Regions by Neutralizing Monoclonal Antibodies," Growth Factors 7:53-64.

Kloth, C. et al. (Sep. 2008). "An Inoculum Expansion Process for Fragile Recombinant CHO Cells Lines," BioProcess International 6(8):44-50.

Kohler, G. et al. (Aug. 7, 1975) "Continuous Cultures of Fused Cells Secreting Antibody of Predefined Specificity," Nature 256:495-497.

Lee, C.V. et al. (2004). "Bivalent Antibody Phage Display Mimics Natural Immunoglobulin," Journal of Immunological Methods 284:119-132.

Lee, C.V. et al. (2004). "High-affinity Human Antibodies From Phage-displayed Synthetic Fab Libraries With a Single Framework Scaffold," J. Mol. Biol. 340(5):1073-1093.

Litton, M.J. et al. (1996). "Antibody-Targeted Superantigen Therapy Induces Tumor-Infiltrating Lymphocytes, Excessive Cytokine Production, and Apoptosis in Human Colon Carcinoma," Eur J. Immunol. 26(1):1-9.

Lonberg, N. et al. (1995, e-pub. Jul. 10, 2009). "Human Antibodies From Transgenic Mice," Int. Rev. Immunol. 13(1):65-93.

Lonberg, N. et al. (Apr. 28, 1994). "Antigen-Specific Human Antibodies From Mice Comprising Four Distinct Genetic Modifications," Nature 368(6474):856-859.

Lorenz, H.-M. et al. (1996). "In Vivo Blockade of TNF-α by Intravenous Infusion of a Chimeric Monoclonal TNF-α Antibody in Patients With Rheumatoid Arthritis: Short Term Cellular and Molecular Effects," J. Immunol. 156(4):1646-1653.

Marks, J.D. et al. (1991). "By-Passing Immunization. Human Antibodies From V-Gene Libraries Displayed on Phage," J. Mol. Biol. 222:581-597.

Marks, J.D. et al. (Jul. 1992). "By-Passing Immunization: Building High Affinity Human Antibodies by Chain Shuffling," Bio/Technology 10:779-783.

Mather, J.P. et al. (1980). "Establishment and Characterization of Two Distinct Mouse Testicular Epithelial Cell Lines," Biology of Reproduction 23:243-252.

Mather, J.P. et al. (1982). "Culture of Testicular Cells in Hormone-Supplemented Serum-Free Medium," Annals New York Academy of Sciences pp. 44-68.

Matsumura, K. et al. (2010). "Polyampholytes as Cryoprotective Agents for Mammalian Cell Cryopreservation," Cell Transplantation 19:691-699.

Morrison, S.L. (Apr. 28, 1994). "Success in Specification," Nature 368:812-813.

Neuberger, M. (Jul. 1996) "Generating High-Avidity Human Mabs in Mice," Nature Biotechnology 14:826, 1 page.

Non Final Office Action, mailed Mar. 6, 2019, for U.S. Appl. No. 15/339,666, filed Jan. 5, 2017, 20 pages.

(56) References Cited

OTHER PUBLICATIONS

Non Final Office Action, mailed Sep. 12, 2019, for U.S. Appl. No. 15/339,666, filed Jan. 5, 2017, 21 pages.
Patkar, A. et al. (2002). "Flow Cytometry as a Useful Tool for Process Development: Rapid Evaluation of Expression Systems," Journal of Biotechnology 93:217-229.
Phelan, M.C. (1996). "Techniques for Mammalian Cell Tissue Culture," in Current Protocols in Molecular Biology Appendix 3F, Supplement 74, pp. A.3F.1-A.3F.18.
Plückthun, A. (1994) "Antibodies from *Escherichia coli*," Chapter 11 in Handbook of Experimental Pharmacology 113:269-315.
Presta, L.G. et al. (Sep. 1, 1993). "Humanization of an Antibody Directed Against IgE," J. Immunol. 151(5):2623-2632.
Richman, C.M. et al. (Dec. 1, 1995). "Radioimmunotherapy for Breast Cancer Using Escalating Fractionated Doses of 131I-Labeled Chimeric L6 Antibody with Peripheral Blood Progenitor Cell Transfusions," Cancer Res. 55(23 Supp):5916s-5920s.
Riechmann, L. et al. (Mar. 24, 1988). "Reshaping Human Antibodies for Therapy," Nature 33(6162):323-327.
Sharkey, R.M. et al. (Dec. 1, 1995). "Evaluation of a Complementarity-Determining Region-Grafted (Humanized) Anti-Carcinoembryonic Antigen Monoclonal Antibody in Preclinical and Clinical Studies," Cancer Res. 55(23Suppl):5935s-5945s.
Sidhu, S.S. et al. (2004). "Phage-Displayed Antibody Libraries of Synthetic Heavy Chain Complementarity Determining Regions," J. Mol. Biol. 338(2):299-310.
St. John, R.C. et al. (Mar. 1993). "Clinical Implications of Basic Research—Immunologic Therapy for ARDS, Septic Shock, and Multiple-Organ Failure," Chest 103(3):932-943.
Stoppa, A.M. et al. (Apr. 1991). "Anti-LFA1 Monoclonal Antibody (25.3) for Treatment of Steroid-Resistant Grade III-IV Acute Graft-Versus-Host Disease," Transplant Intl. 4(1):3-7.
Urlaub, G. et al. (Jul. 1980). "Isolation of Chinese Hamster Cell Mutants Deficient in Dihydrofolate Reductase Activity," Proc. Natl. Acad. Sci. USA 77(7):4216-4220.
Vijayasankaran, N. et al. (2005; e-published on Dec. 30, 2004). "Synthesis of poly[®-3-hydroxybutyric Acid) in the Cytoplasm of Pichia Pastoris under Oxygen Limitation," Biomacromolecules 6(2):604:611.
Written Opinion for PCT Application No. PCT/US2015/039757, mailed on Oct. 22, 2015, filed on Jul. 9, 2015, 7 pages.
Yazaki, P.J. et al. (2004). "Expression of Recombinant Antibodies in Mammalian Cell Lines," Chapter 15 in Methods in Molecular Biology, Lo, B.K.C. (ed.), Humana Press, Totowa, NJ, 248:255-268.
Zhou, H. et al. (May-Jun. 2010, e-pub. Dec. 28, 2009). "pH Measurement and a Rational and Practical pH Control Strategy for High Throughput Cell Culture System," American Institute of Chemical Engineers Biotechnol. Prog. 26(3):872-880.

\* cited by examiner

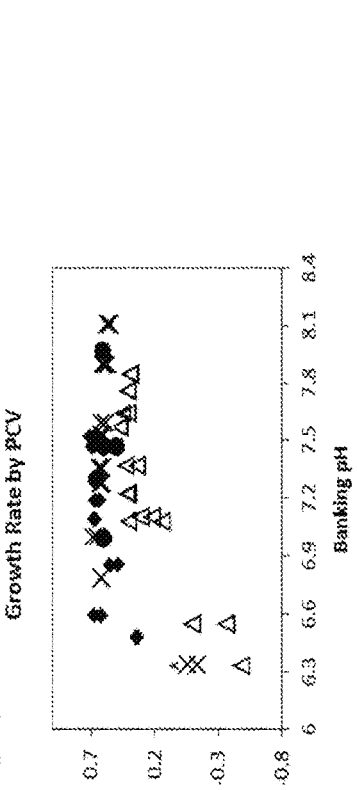
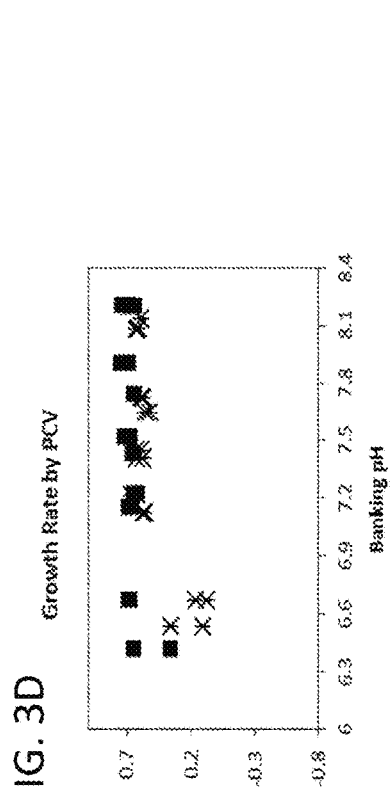
FIG. 3A  FIG. 3B
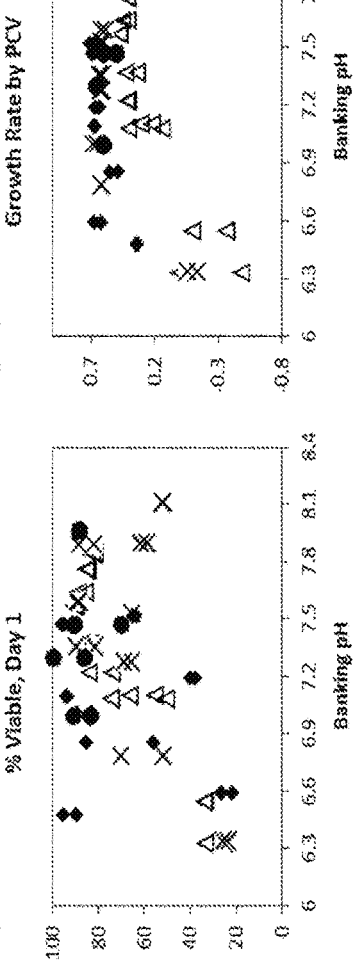
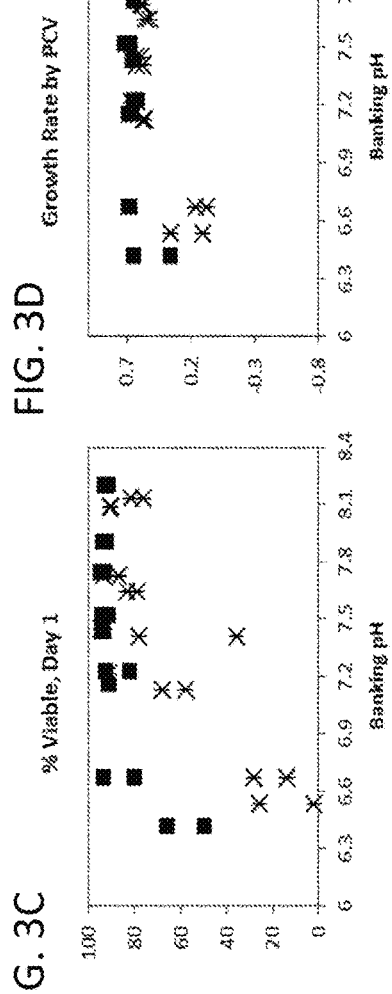
FIG. 3C  FIG. 3D
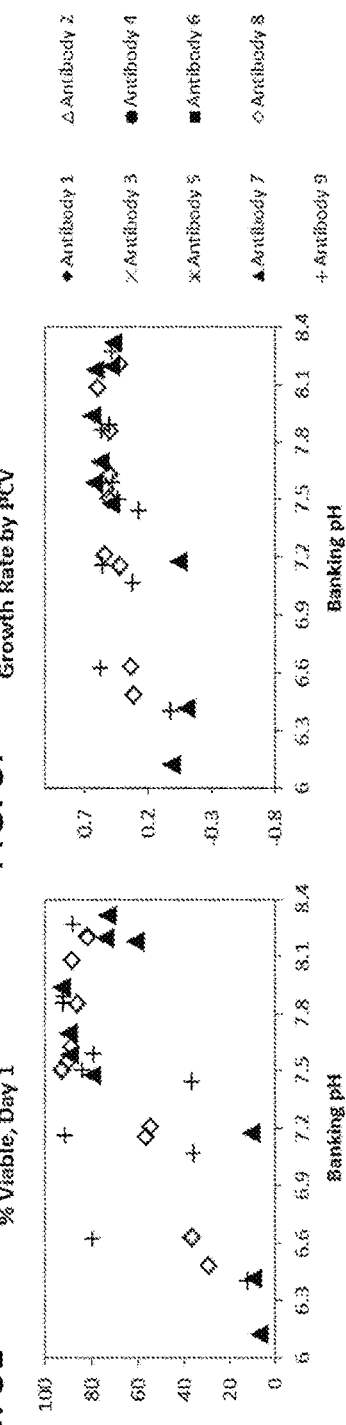
FIG. 3E  FIG. 3F

PH ADJUSTMENT TO IMPROVE THAW RECOVERY OF CELL BANKS

CROSS-REFERENCE TO RELATED APPLICATIONS

This Application is a divisional of U.S. patent application Ser. No. 16/798,014, filed Feb. 21, 2020, which is a divisional of U.S. patent application Ser. No. 15/399,666, filed on Jan. 5, 2017, now U.S. Pat. No. 10,602,739, which is a continuation application of International Application No. PCT/US2015/039757, filed on Jul. 9, 2015, which claims the priority benefit of U.S. provisional application Ser. No. 62/022,392, filed on Jul. 9, 2014, each of which is incorporated herein by reference in its entirety.

FIELD OF THE INVENTION

The present invention relates to methods of freezing cells (such as mammalian cells) for banking and freezing media for use in freezing cells.

BACKGROUND OF THE INVENTION

Cell banks are produced by first accumulating cells in a batch/perfusion cell culture process and then harvesting cells for banking. The process involves three stages: cell accumulation, harvest and cell concentration, and cell banking. A harvest process step serves to concentrate the final cell culture fluid or to extract the cells from the cell culture fluid using centrifugation. A subsequent pooling and filling process serves to prepare cell bank ampoules for long-term storage.

These traditional methods may result in inconsistent or poor viability post-thaw for select cell lines. Imperative to the cell banking process is the need for high cell viability after thawing of the frozen cells. Thus, improved methods of freezing cells for cell banking are desirable. Cell culture medium for freezing cells that allows for greater cell viability when thawed after banking would be beneficial.

All publications, patents, and patent applications cited herein are hereby incorporated by reference in their entirety for all purposes.

BRIEF SUMMARY OF THE INVENTION

In one aspect, provided herein is a method of improving thaw recovery of cell banks comprising freezing eukaryotic cells (e.g., mammalian cells, insect cells, etc.) for banking in a freezing medium, wherein the freezing medium comprises a buffered solution and a cryoprotective agent, and wherein the freezing medium has a pH of about 6.7 to about 8.5 prior to freezing or has been adjusted to a pH of about 6.7 to about 8.5 prior to freezing.

In another aspect, provided herein is a method of freezing eukaryotic cells (e.g., mammalian cells, insect cells, etc.) for storage comprising freezing the cells in a freezing medium, wherein the freezing medium comprises a buffered solution and a cryoprotective agent, and wherein the freezing medium has a pH of about 6.7 to about 8.5 prior to freezing or has been adjusted to a pH of about 6.7 to about 8.5 prior to freezing.

In some embodiments of the methods described above or herein, the freezing medium has a pH of about 6.7 to about 8.3, about 6.8 to about 8.3, about 6.9 to about 8.3, about 7.0 to about 8.3, about 7.1 to about 8.3, about 7.2 to about 8.3, about 7.3 to about 8.3, about 7.4 to about 8.3, about 7.5 to about 8.3, about 7.2 to about 8.0, about 7.2 to about 7.8, or about 7.5 prior to freezing.

In some embodiments of the methods described above or herein, the pH of the freezing medium has been adjusted to a pH of about 6.7 to about 8.5, about 6.7 to about 8.3, about 6.8 to about 8.3, about 6.9 to about 8.3, about 7.0 to about 8.3, about 7.1 to about 8.3, about 7.2 to about 8.3, about 7.3 to about 8.3, about 7.4 to about 8.3, about 7.5 to about 8.3, about 7.2 to about 8.0, about 7.2 to about 7.8, or about 7.5. In some embodiments of the methods described above or herein, the cells (e.g., mammalian cells or insect cells) are combined with a freezing medium before and/or after pH adjustment. In some embodiments, the adjusted pH is a target pH or a measured pH. In some embodiments, the target pH is about 6.7 to about 8.5, or any of the pH or in any pH ranges described herein. In some embodiments, the measured pH is about 6.7 to about 8.5, or any of the pH or in any pH ranges described herein. In some embodiments of the methods described above or herein, the method further comprises a step of measuring an initial pH of the freezing medium containing the cells (e.g., mammalian cells or insect cells) prior to adjusting pH of the freezing medium. In some embodiments of the methods described above or herein, the method further comprises a step of measuring the adjusted pH of the freezing medium. In some embodiments of the methods described above or herein, if the measured pH of the freezing medium is below a target pH, the method comprises repeating the adjusting step and measuring step until the adjusted pH of the freezing medium is about 6.7 to about 8.5, or any of the pH or in any pH ranges described herein.

In some embodiments of the methods described herein or above, the pH is adjusted by adding a base. In some embodiments, the base is selected from the group consisting of sodium carbonate, sodium bicarbonate, HEPES (4-(2-hydroxyethyl)-1-piperazineethanesulfonic acid) sodium salt, sodium hydroxide, and potassium hydroxide. In some embodiments, the pH of the freezing medium is adjusted by adding a base to the freezing medium according to the following formula $V_{base}=C_{base}*V_p (pH_t-pH_i)$, wherein $C_{base}$ is a base-specific coefficient, $V_{base}$ is a volume of the base to add to the freezing medium, $V_p$ is the volume of the freezing medium, $pH_t$ is the target pH, and $pH_i$ is the initial pH. In some embodiments, the pH of the freezing medium is adjusted by adding sodium carbonate to the freezing medium according to the following formula $V_{Na2CO3}=0.0085V_p (pH_t-pH_i)$, wherein $V_{Na2CO3}$ is a volume of 1M sodium carbonate to add to the freezing medium, $V_p$ is the volume of the freezing medium, $pH_t$ is the target pH, and $pH_i$ is the initial pH. In some embodiments, the target pH is a pH between about 6.7 to about 8.5, about 7.2 to about 8.3, or any of the pH or in any pH ranges described herein. In some embodiments, the target pH is 7.5.

In some embodiments of the methods described above or herein, the cells (e.g., mammalian cells or insect cells) are in a medium having a pH of about 6.2 to about 6.6 before the cells are combined with a freezing medium.

In some embodiments of the methods described above or herein, the cryoprotective agent is DMSO (dimethyl sulfoxide), glycerol, propanediol, ethylene glycol, a macromolecule, a sugar, or a combination thereof. In some embodiments, the DMSO or glycerol in the freezing medium prior to freezing is at a concentration of about 5% to about 12.5% by volume. In some embodiments, the DMSO or glycerol in the freezing medium prior to freezing the cells (e.g., mammalian cells or insect cells) is at a concentration of about 5% to about 10% by volume.

In some embodiments of the methods described above or herein, the freezing medium containing the cells (e.g., mammalian cells or insect cells) has a cell density of about 8% to about 28% packed cell volume (PCV) prior to freezing.

In some embodiments of the method described above or herein, the method further comprises a step of cooling cell culture fluid during cell harvest and concentration process before the cells (e.g., mammalian cells or insect cells) are combined with a freezing medium. In some embodiments, the cell culture fluid is cooled to a temperature at or below about 20° C. In some embodiments, the cell culture fluid is cooled to a temperature at or below about 10° C.

In another aspect, provided here is a method of freezing eukaryotic cells (e.g., mammalian cells, insect cells, etc.) for storage or improving thaw recovery of cell banks comprising (a) adjusting pH of a freezing medium containing cells to a pH of about 6.7 to about 8.5, wherein the freezing medium comprises a buffered solution and a cryoprotective agent; and (b) freezing the cells.

In some embodiments, the pH is adjusted to a pH of about 6.7 to about 8.3, about 6.8 to about 8.3, about 6.9 to about 8.3, about 7.0 to about 8.3, about 7.1 to about 8.3, about 7.2 to about 8.3, about 7.3 to about 8.3, about 7.4 to about 8.3, about 7.5 to about 8.3, about 7.2 to about 8.0, about 7.2 to about 7.8, or about 7.5. In some embodiments, the adjusted pH is a target pH or a measured pH. In some embodiments, the target pH is about 6.7 to about 8.5, or any of the pH or in any pH ranges described herein. In some embodiments, the target pH is about 7.5. In some embodiments, the measured pH is about 6.7 to about 8.5, or any of the pH or in any pH ranges described herein.

In some embodiments of the methods described above or herein, the method further comprises a step of measuring an initial pH of the freezing medium containing the cells (e.g., mammalian cells or insect cells) prior to adjusting pH of the freezing medium. In some embodiments, the method further comprises a step of measuring the adjusted pH of the freezing medium. In some embodiments, if the measured pH of the freezing medium is below a target pH, the method comprises repeating the adjusting step and measuring step until the adjusted pH of the freezing medium is about 6.7 to about 8.5, about 7.2 to about 8.3, or any of the pH or in any pH ranges described herein.

In some embodiments of the methods described above or herein, the pH is adjusted by adding a base. In some embodiments, the base is selected from the group consisting of sodium carbonate, sodium bicarbonate, HEPES sodium salt, sodium hydroxide, and potassium hydroxide. In some embodiments, the pH of the freezing medium is adjusted by adding a base to the freezing medium according to the following formula $V_{base} = C_{base} * V_p (pH_t - pH_i)$, wherein $C_{base}$ is a base-specific coefficient, $V_{base}$ is a volume of the base to add to the freezing medium, $V_p$ is the volume of the freezing medium, $pH_t$ is the target pH, and $pH_i$ is the initial pH. In some embodiments, the pH of the freezing medium is adjusted by adding sodium carbonate to the freezing medium according to the following formula $V_{Na2CO3} = 0.0085 V_p (pH_t - pH_i)$, wherein $V_{Na2CO3}$ is a volume of 1M sodium carbonate to add to the freezing medium, $V_p$ is the volume of the freezing medium, $pH_t$ is the target pH, and $pH_i$ is the initial pH. In some embodiments, the target pH is about 6.7 to about 8.5, or any of the pH or in any pH ranges described herein. In some embodiments, the target pH is about 7.5.

In some embodiments, the cells (e g , mammalian cells or insect cells) are in a medium having a pH of about 6.2 to about 6.6 before the cells are combined with a freezing medium.

In some embodiments, the cryoprotective agent in the freezing medium is DMSO, glycerol, propanediol, ethylene glycol, a macromolecule, a sugar, or a combination thereof. In some embodiments, the DMSO or glycerol in the freezing medium containing the cells (e.g., mammalian cells or insect cells) prior to freezing is at a concentration of about 5% to about 12.5% by volume. In some embodiments, the DMSO or glycerol in the freezing medium containing the cells (e.g., mammalian cells or insect cells) prior to freezing the cells is at a concentration of about 5% to about 10% by volume.

In some embodiments, the freezing medium containing the cells (e.g., mammalian cells or insect cells) has a cell density of about 8% to about 28% packed cell volume (PCV) prior to freezing.

In some embodiments, the method further comprises a step of cooling cell culture fluid during cell harvest and concentration process before the cells (e.g., mammalian cells or insect cells) are combined with a freezing medium. In some embodiments, the cell culture fluid is cooled to a temperature at or below about 20° C., or at or below about 10° C.

In another aspect, provided herein is a method of freezing eukaryotic cells (e.g., mammalian cells, insect cells, etc.) for storage or improving thaw recovery of cell banks comprising (a) adjusting pH of a freezing medium to a pH of about 6.7 to about 8.5, wherein the freezing medium comprises a buffered solution and a cryoprotective agent; (b) combining the cells with the freezing medium to form a cell pool; and (c) freezing the cells in the cell pool.

In some embodiments, the pH is adjusted to a pH of about 6.7 to about 8.3, about 6.8 to about 8.3, about 6.9 to about 8.3, about 7.0 to about 8.3, about 7.1 to about 8,3, about 7.2 to about 8.3, about 7.3 to about 8.3, about 7.4 to about 8.3, about 7.5 to about 8.3, about 7.2 to about 8.0, about 7.2 to about 7.8, or about 7.5. In some embodiments, the adjusted pH is a target pH or a measured pH. In some embodiments, the target pH is about 6.7 to about 8.5, or any of the pH or in any pH ranges described herein. In some embodiments, the measured pH is about 6.7 to about 8.5, or any of the pH or in any pH ranges described herein.

In some embodiments, the method further comprises a step of measuring the adjusted pH of the freezing medium. In some embodiments, if the measured pH of the freezing medium is below a target pH, the method further comprises repeating the adjusting step and measuring step until the adjusted pH of the freezing medium is about 6.7 to about 8.5, or any of the pH or in any pH ranges described herein.

In some embodiments of the methods described above or herein, the pH is adjusted by adding a base. In some embodiments, the base is selected from the group consisting of sodium carbonate, sodium bicarbonate, HEPES sodium salt, sodium hydroxide, and potassium hydroxide.

In some embodiments of the methods described above or herein, the cells (e.g., mammalian cells or insect cells) are in a medium having a pH of about 6.2 to about 6.6 before the cells are combined with a freezing medium.

In some embodiment of the methods described above or herein, the cryoprotective agent in the freezing medium is DMSO, glycerol, propanediol, ethylene glycol, a macromolecule, a sugar, or a combination thereof. In some embodiment, the DMSO or glycerol in the cell pool is at a concentration of about 5% to about 12.5% by volume, or about 5% to about 10% by volume.

In some embodiments of the methods described above or herein, the cell pool contains the cells (e.g., mammalian cells or insect cells) at a cell density of about 8% to about 28% packed cell volume (PCV).

In some embodiments of the methods described above or herein, the method further comprises a step of cooling cell culture fluid during cell harvest and concentration process before the cells (e.g., mammalian cells or insect cells) are combined with a freezing medium. In some embodiments, the cell culture fluid is cooled to a temperature at or below about 20° C. In some embodiments, the cell culture fluid is cooled to a temperature at or below about 10° C.

In some embodiments of the methods described above or herein, the cells are mammalian cells, such as Chinese hamster ovary (CHO) cells, NS0 murine myeloma cells, PER.C6® human cells, or hybridomas. In some embodiments, the cells are insect cells, such as High Five™, S2 (Schneider 2), Sf9, and Sf21. In some embodiments of the methods described above or herein, the cells (e.g., mammalian cells or insect cells) comprise a nucleic acid encoding a polypeptide. In some embodiments, the polypeptide is a therapeutic protein. In some embodiments, the therapeutic protein is selected from the group consisting of an antibody, an antibody fragment, an enzyme, and a receptor fusion protein.

In another aspect, provided herein is an eukaryotic cell pool (e.g., a mammalian cell pool, or an insect cell pool) for freezing cells comprising a buffered solution, a cryoprotective agent, and eukaryotic cells comprising a nucleic acid encoding a polypeptide, wherein the medium has a pH of about 6.7 to about 8.5 or about 7.2 to about 8.3 (or any of the pH or in any pH ranges described herein) prior to freezing the cells. In some embodiments, the cells are mammalian cells, such as Chinese hamster ovary (CHO) cells, NS0 murine myeloma cells, PER.C6® human cells, or hybridomas. In some embodiments, the cells are insect cells, such as High Five™, S2 (Schneider 2), Sf9, and Sf21. In some embodiments, the cells (e.g., mammalian cells or insect cells) comprise a nucleic acid encoding a polypeptide. In some embodiments, the polypeptide is a therapeutic protein. In some embodiments, the therapeutic protein is selected from the group consisting of an antibody, an antibody fragment, an enzyme, and a receptor fusion protein.

In another aspect, provided herein is a cell bank comprising a plurality of containers and each container contains (a) a freezing medium comprising a buffer and a cryoprotective agent, and (b) eukaryotic cells (e.g., mammalian cells or insect cells) comprising a nucleic acid encoding a polypeptide, wherein the freezing medium has a pH of about 6.7 to about 8.5 or about 7.2 to about 8.3 (or any of the pH or in any pH ranges described herein) prior to freezing the cell. In some embodiments, the containers are ampoules. In some embodiments, the cells are mammalian cells, such as Chinese hamster ovary (CHO) cells, NS0 murine myeloma cells, PER.C6® human cells, or hybridomas. In some embodiments, the cells are insect cells, such as High Five™, S2 (Schneider 2), Sf9, and Sf21. In some embodiments, the cells (e.g., mammalian cells or insect cells) comprise a nucleic acid encoding a polypeptide. In some embodiments, the polypeptide is a therapeutic protein. In some embodiments, the therapeutic protein is selected from the group consisting of an antibody, an antibody fragment, an enzyme, and a receptor fusion protein.

It is to be understood that one, some, or all of the properties of the various embodiments described herein may be combined to form other embodiments of the present invention. These and other aspects of the invention will become apparent to one of skill in the art.

BRIEF DESCRIPTION OF THE DRAWINGS

FIGS. 3A-3F show thaw passage day 1 viability (FIGS. 3A, 3C, and 3E) and overall growth rate by PCV (FIGS. 3B, 3D, and 3F) vs. banking pH and the effect of adjusting pH to a range of pH targets across nine CHO cell lines each producing a different antibody (antibodies 1-9).

DETAILED DESCRIPTION

Figure 1:
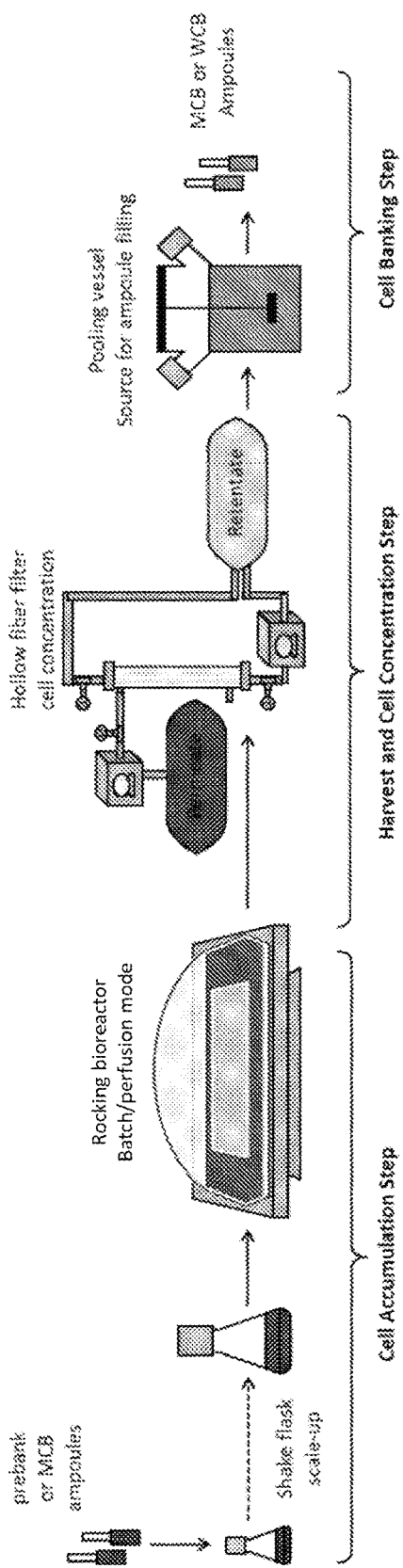
FIG. 1 shows an example of a cell banking process flow.

Provided herein are methods of improving thaw recovery of cell banks comprising freezing eukaryotic cells (e.g., mammalian cells, insect cells, etc.) for banking in a freezing medium, wherein the freezing medium comprises a buffered solution and a cryoprotective agent, and wherein the freezing medium has a pH of about 6.7 to about 8.5 prior to freezing.

Also provided herein are methods of freezing eukaryotic cells (e.g., mammalian cells, insect cells, etc.) for storage comprising freezing the cells in a freezing medium, wherein the freezing medium comprises a buffered solution and a cryoprotective agent, and wherein the freezing medium has a pH of about 6.7 to about 8.5 prior to freezing.

Also provided herein are methods of freezing eukaryotic cells (e.g., mammalian cells, insect cells, etc.) for storage or improving thaw recovery of cell banks comprising (a) adjusting pH of a freezing medium containing the cells to a pH of about 6.7 to about 8.5, wherein the freezing medium comprises a buffered solution and a cryoprotective agent; and (b) freezing the cells.

Also provided herein are methods of freezing eukaryotic cells (e.g., mammalian cells, insect cells, etc.) for storage or improving thaw recovery of cell banks comprising (a) adjusting pH of a freezing medium to a pH of about 6.7 to about 8.5, wherein the freezing medium comprises a buffered solution and a cryoprotective agent; (b) combining the cells with the freezing medium to form a cell pool; and (c) freezing the cells in the cell pool.

Also provided herein are eukaryotic cell pools for freezing eukaryotic cells (e.g., mammalian cells, insect cells, etc.) comprising a buffered solution, a cryoprotective agent, and eukaryotic cells comprising a nucleic acid encoding a polypeptide, wherein the medium has a pH of about 6.7 to about 8.5 prior to freezing the cells.

Also provided herein are cell banks comprising a plurality of containers and each container contains (a) a freezing medium comprising a buffer and a cryoprotective agent, and (b) eukaryotic cells (e.g., mammalian cells, insect cells, etc.) comprising a nucleic acid encoding a polypeptide, wherein the freezing medium has a pH of about 6.7 to about 8.5 prior to freezing the cell.

I. Definitions

The terms "medium" and "cell culture medium" refer to a solution used for maintaining cells. The medium may further comprise a nutrient source used for growing cells. As is understood by a person of skill in the art, the nutrient source may contain components required by the cell for growth and/or survival or may contain components that aid in cell growth and/or survival. Vitamins, essential or non-essential amino acids, and trace elements are examples of medium components.

A "basal nutrient medium" refers to a medium comprising the basic nutrients required for cell growth and survival. Examples of a basal nutrient medium include Eagle's Minimum Essential Medium (EMEM) and Dulbecco's Modified Eagle's Medium (DMEM).

A "chemically defined cell culture medium" or "CDM" is a medium with a specified composition that is free of products derived from animal or plant such as for example animal serum and plant peptone. As would be understood by a person of skill in the art, a CDM may be used in a process of polypeptide production whereby a cell is in contact with, and secretes a polypeptide into, the CDM. Thus, it is understood that a composition may contain a CDM and a polypeptide product and that the presence of the polypeptide product does not render the CDM chemically undefined.

A "chemically undefined cell culture medium" refers to a medium whose chemical composition cannot be specified and which may contain one or more products derived from animal or plant sources, for example animal serum or plant peptone. As would be understood by a person of skill in the art, a chemically undefined cell culture medium may contain a product derived from an animal or a plant as a nutrient source.

A "freezing medium", "cell freezing medium" or "cell culture medium for freezing" refers to a buffered solution containing a cryoprotective agent. A freezing medium may be used for freezing cells (e.g., mammalian cells or insect cells) contained in the freezing medium. A "buffered solution", as used herein, refers to a water-based, isotonic, pH buffered salt solution, which acts to preserve the integrity of the cell membrane and serves as a carrier for one or more cryoprotective agents. A freezing medium may also contain additional components found in cell culture medium. Examples of buffers may include bicarbonate buffer, PBS (phosphate buffered saline), HEPES (4-(2-hydroxyethyl)-1-piperazineethanesulfonic acid), MOPS (3-(N-morpholino) propanesulfonic acid), TES (N-[tris(hydroxymethyl)methyl]-2-aminoethanesulfonic acid), TRIS (tris(hydroxymethyl)aminomethane), TEST (TES/TRIS combo), and a combination thereof. Examples of medium may include Eagle's Minimum Essential Medium (EMEM) and Dulbecco's Modified Eagle's Medium (DMEM). Cryoprotective agents protect cells from freezing damage and may be classified as "permeating", able to cross the plasma membrane (e.g., glycerol, dimethyl sulfoxide (DMSO), propanediol, ethylene glycol, etc.), or "non-permeating" (e.g., macromolecules, sugars, etc.).

"Culturing" a cell refers to contacting a cell with a cell culture medium under conditions suitable to the survival and/or growth and/or proliferation of the cell.

"Batch culture" refers to a culture in which all components for cell culturing (including the cells and all culture nutrients) are supplied to the culturing vessel at the start of the culturing process.

The phrase "fed batch cell culture," as used herein refers to a batch culture wherein the cells and culture medium are supplied to the culturing vessel initially, and additional culture nutrients are fed, continuously or in discrete increments, to the culture during the culturing process, with or without periodic cell and/or product harvest before termination of culture.

"Perfusion culture" is a culture by which the cells are restrained in the culture by, e.g., filtration, encapsulation, anchoring to microcarriers, etc., and the culture medium is continuously or intermittently introduced and removed from the culturing vessel.

"Cell banking" or "banking" is a process by which cells are frozen to sub-zero temperatures (cryopreserved) to halt enzymatic/chemical reactions, thus maintaining cells in a viable state for later use. The frozen cells may be stored at less than about 0° C. (e.g., at −20° C., −70° C., −80° C., or lower) for later use. For example, cells may be stored in ampoules placed in the vapor phase within a freezer containing liquid nitrogen at −196° C.

"Culturing vessel" refers to a container used for culturing a cell. The culturing vessel can be of any size so long as it is useful for the culturing of cells.

The term "titer" as used herein refers to the total amount of recombinantly expressed polypeptide produced by a cell culture divided by a given amount of medium volume. Titer is typically expressed in units of milligrams of polypeptide per milliliter of medium.

A "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer.

An "isolated nucleic acid" means and encompasses a non-naturally occurring, recombinant or a naturally occurring sequence outside of or separated from its usual context. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the protein where, for example, the nucleic acid molecule is in a chromosomal location different from that of natural cells.

An "isolated" protein (e.g., an isolated antibody) is one which has been identified and separated and/or recovered from a component of its natural environment. Contaminant components of its natural environment are materials which would interfere with research, diagnostic or therapeutic uses for the protein, and may include enzymes, hormones, and other proteinaceous or nonproteinaceous solutes. Isolated protein includes the protein in situ within recombinant cells since at least one component of the protein's natural environment will not be present. Ordinarily, however, isolated protein will be prepared by at least one purification step.

A "purified" polypeptide means that the polypeptide has been increased in purity, such that it exists in a form that is more pure than it exists in its natural environment and/or when initially produced and/or synthesized and/or amplified under laboratory conditions. Purity is a relative term and does not necessarily mean absolute purity.

"Contaminants" refer to materials that are different from the desired polypeptide product. The contaminant includes, without limitation: host cell materials, such as host cell protein; nucleic acid; a variant, fragment, aggregate or derivative of the desired polypeptide; another polypeptide; endotoxin; viral contaminant; cell culture media component, etc. Contaminants may also include materials introduced by purification process, such as leached Protein A.

The terms "polypeptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Examples of polypeptides encompassed within the definition herein include mammalian proteins, such as, e.g., renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-b; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and (IGF-I and IGF-II); des(1-3)-IGF-I (brain IGF-I), insulin-like growth factor binding proteins (IGFBPs); CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as CA125 (ovarian cancer antigen) or HER2, HER3 or HER4 receptor; immunoadhesins; and fragments and/or variants of any of the above-listed proteins as well as antibodies, including antibody fragments, binding to a protein, including, for example, any of the above-listed proteins.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. An antibody can be human, humanized and/or affinity matured.

The term "monoclonal antibody" as used herein refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they can be synthesized uncontaminated by other antibodies. The modifier "monoclonal" is not to be construed as requiring production of the antibody by any particular method. For example, the monoclonal antibodies to be used in accordance with the invention may be made by a variety of techniques, including, for example, the hybridoma method (e.g., Kohler and Milstein, *Nature,* 256:495-97 (1975); Hongo et al., *Hybridoma,* 14 (3): 253-260 (1995), Harlow et al., *Antibodies: A Laboratory Manual,* (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods in bacterial, eukaryotic animal or plant cells (see, e.g., U.S. Pat. No. 4,816,567); phage-display technologies (see, e.g., Clackson et al., *Nature,* 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004) and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile.

"Pharmaceutically acceptable" carriers, excipients, or stabilizers are ones which are nontoxic to the cell or mammal being exposed thereto at the dosages and concentrations employed (Remington's Pharmaceutical Sciences (20$^{th}$ edition), ed. A. Gennaro, 2000, Lippincott, Williams & Wilkins, Philadelphia, PA). Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, polyethylene glycol (PEG), and Pluronics™.

As used in this specification and the appended claims, the singular forms "a", "an" and "the" include plural referents unless the content clearly dictates otherwise. Thus, for example, reference to "a compound" optionally includes a combination of two or more such compounds, and the like.

It is understood that aspect and embodiments of the invention described herein include "comprising," "consisting," and "consisting essentially of" aspects and embodiments.

Reference to "about" a value or parameter herein includes (and describes) embodiments that are directed to that value or parameter per se. For example, description referring to "about X" includes description of "X." Numeric ranges are inclusive of the numbers defining the range.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

II. Methods and Uses of the Invention

Provided herein are methods of freezing cells for banking or storage in a cell freezing medium. Also provided herein are methods of improving thaw recovery of cell banks. Methods comprise a step of freezing cells in a freezing medium, wherein the freezing medium comprises a buffered solution and a cryoprotective agent, and wherein the freezing medium containing the cells has a pH of about 6.7 to about 8.5 or about 6.7 to about 8.3 prior to freezing. The methods may further comprise a step of adjusting the pH of the freezing medium to about 6.7 to about 8.5 or about 6.7 to about 8.3. The methods provided herein are useful for preparing master cell banks (MCBs) and working cell banks (WCBs). In some embodiments, the methods described herein improve cell viability and/or cell growth after thawing.

Eukaryotic cells (e.g., mammalian cells, insect cells, etc.) to be used in freezing and banking process may be prepared by a process involving cell culture and concentration protocols known in the art. The method may include cell accumulation, harvest, and cell concentration before cell banking. Cell accumulation may occur by several methods. One example may use a process controlled bioreactor for cell accumulation; however, other methods/culture vessels may be used as well (e.g. T-flasks, shake flasks, roller bottles, spinner vessels, etc.). Harvest and cell concentration may be performed by centrifugation followed by resuspension of the cell pellet in a freezing medium. In another example, cells may be harvested and concentrated in a single step via a hollow fiber filter (HFF). Cell concentration may also be achieved by use of alternative perfusion membrane/devices to remove medium from cell culture fluid (e.g. floating perfusion membranes, cell settlers, continuous circulating centrifuges, etc.). In some embodiments of the method described herein, the harvesting and cell concentration process or the harvested cell culture fluid is cooled to a temperature at or below about 20° C. (e.g., at or below about any of 19° C., 18° C., 17° C., 16° C., 15° C., 14° C., 13° C., 12° C., 11° C., and 10° C.).

Pelleted or concentrated cells may then be combined with a freezing medium before freezing the cells. In some embodiments, pelleted cells can be resuspended in a freezing medium. In some embodiments, a freezing medium containing concentrated cryoprotective agent can be added into the harvested and concentrated cells or the harvested and concentrated cells can be added into a freezing medium containing concentrated cryoprotective agent for cell banking. A freezing medium may comprise a buffer solution and a cryoprotective agent. In some embodiments, the buffer in the medium may comprise a zwitterionic buffer. In some embodiments, the buffer in the medium may comprise a buffer selected from bicarbonate buffer, PBS (phosphate buffered saline), HEPES (4-(2-hydroxyethyl)-1-piperazineethanesulfonic acid), MOPS (3-(N-morpholino)propanesulfonic acid), TES (N-[tris(hydroxymethyl)methyl]-2-aminoethanesulfonic acid), TRIS (tris(hydroxymethyl) aminomethane), TEST (TES/TRIS combo), and a combination thereof. In some embodiments, buffer concentration in the freezing medium before freezing the cells is about 10 mM to about 50 mM. In some embodiments, the freezing medium before freezing the cells contains about 10 mM to about 35 mM sodium bicarbonate (e.g., about 10 mM, about 15 mM, about 20 mM, about 25 mM, about 30 mM, or about 35 mM, including any concentration in between these values). In some embodiments, the freezing medium before freezing the cells contains about 10 mM to about 50 mM HEPES (e.g., about 10 mM, about 15 mM, about 20 mM, about 25 mM, about 30 mM, about 35 mM, about 40 mM, about 45 mM, or about 50 mM, including any concentration in between these values). In some embodiments, the freezing medium before freezing the cells contains about 10 mM to about 12 mM PBS (e.g., about 10 mM, about 11 mM, or about 12 mM, including any concentration in between these values). In some embodiments, the freezing medium before freezing the cells contains about 10 mM to about 20 mM MOPS (e.g., about 10 mM, about 12 mM, about 15 mM, about 18 mM, or about 20 mM, including any concentration in between these values). In some embodiments, the freezing medium before freezing the cells contains about 10 mM to about 30 mM TES (e.g., about 10 mM, about 15 mM, about 20 mM, about 25 mM, or about 30 mM, including any concentration in between these values). In some embodiments, the freezing medium before freezing the cells contains about 10 mM to about 30 mM TRIS (e.g., about 10 mM, about 15 mM, about 20 mM, about 25 mM, or about 30 mM, including any concentration in between these values). In some embodiments, the freezing medium before freezing the cells contains about 10 mM to about 30 mM TEST (e.g., about 10 mM, about 15 mM, about 20 mM, about 25 mM, or about 30 mM, including any concentration in between these values). In some embodiments, a cryoprotective agent is a permeating agent or a non-permeating agent. In some embodiments, a cryoprotective agent is an agent selected from a group consisting of glycerol, dimethylsulfoxide (DMSO), propanediol, ethylene glycol, and sugars. In some embodiments, the freezing medium added into the harvested and concentrated cells is a concentrated freezing medium. In some embodiments, the freezing medium containing concentrated cryoprotective agent may contain 20-30% (v/v) dimethylsulfoxide (DMSO) or glycerol. In some embodiments, the concentrated freezing medium is poured (e.g., 1 part freezing medium (containing concentrated cryoprotective agent) volume:3 parts cell culture fluid) into the harvested and concentrated cells. In some embodiments, the freezing medium containing the cells before freezing the cells contains about 5% to about 12.5% of DMSO or glycerol.

In some embodiments, a freezing medium may further comprise additional components found in cell culture medium. In some embodiments, the freezing medium may contain Eagle1's Minimum Essential Medium (EMEM) or Dulbecco's Modified Eagle's Medium (DMEM).

In some embodiments, the method of preparing a cell (such as a mammalian cell or an insect cell) for freezing may further comprise a step of adjusting the pH of a freezing medium or a freezing medium containing concentrated cryoprotective agent, wherein the pH is adjusted to about 6.7 to about 8.5 before the pelleted cells or concentrated cells are combined with the freezing medium or the freezing medium containing concentrated cryoprotective agent. In some embodiments, the method of preparing cells (such as mammalian cells or insect cells) for freezing further comprises a step of adjusting the pH of the freezing medium containing the cells, wherein the pH of the freezing medium is adjusted to about 6.7 to about 8.5. In some embodiments, the adjusted pH is a target pH or a measured pH.

In certain embodiments, the cell density prior to freezing is measured by packed cell volume (PCV). In some embodiments, the freezing medium comprising cells to be banked has a cell density of 8% to 28% (e.g., about any of 8%, 10%, 15%, 20%, 25% or 28%) PCV prior to freezing. In some embodiments, the cell density in the freezing medium before freezing may be about 21% PCV.

In some embodiments, the cells in a freezing medium are dispensed into ampoules or single-use bags prior to freezing. In an exemplary embodiment, the process involves: dispensing the cell suspension into autoclaved glass ampoules that are placed on wet ice using an autoclaved self-filling syringe, sealing the ampoules, performing an integrity test, and freezing ampoules in a rate-controlled freezer and then transferring ampoules to a liquid nitrogen freezer for long term storage.

In some embodiments, the cell viability after thawing is improved by using the methods described herein. In some embodiments, the cell viability is increased by at least about any of 10%, 15%, 20%, 25%, 30%, 35%, 40%, 45%, 50%, 55%, 60%, 65%, 70%, 75%, or 85% as compared to the cell viability after frozen in a freezing medium with a pH of 6.7 or lower and/or without cooling the harvest cell culture during the harvesting process and thawing.

pH Adjustment

According to the methods as described herein, the pH of the freezing medium (containing or not containing the cells) may be adjusted, for example, by adding a base to the medium. In some embodiments, the pH of the freezing medium is adjusted to a pH that is above about 6.7. In some embodiments, the pH of the freezing medium is adjusted to a pH (a target pH or a measured pH) between about 6.7 and about 8.5. In some embodiments, the pH of the freezing media is adjusted to a pH between about 6.8 to about 8.3, between about 6.9 to about 8.3, between about 7.0 to about 8.3, between about 7.1 to about 8.3, between about 7.2 to about 8.3, between about 7.3 to about 8.3, between about 7.4 to about 8.3, between about 7.5 to about 8.3, between about 7.6 to about 8.3, between about 7.7 to about 8.3, or between about 7.8 to about 8.3 In some embodiments, the pH of the freezing media is adjusted to a pH (a target pH or a measured pH) between about 7.2 to about 7.8. In some embodiments, the target pH or measured pH is about 7.2 to about 8.3. In some embodiments, the target pH or measured pH is about 7.2 to about 7.8 (e.g. pH of about 7.5). In some embodiments, if the first pH adjustment is not sufficient to increase the pH to be with the target pH range (e.g., pH of about 7.3 to about 7.7), a second pH adjustment is performed. In some embodiments, more than one pH adjustments may be performed.

The base added to adjust the pH may be any base that is well known to those skilled in the art, but in exemplary embodiments, the base is sodium carbonate, sodium bicarbonate, HEPES sodium salt, sodium hydroxide, or potassium hydroxide.

The pH of the freezing media may be measured at any point prior to freezing and the pH may be adjusted at any time prior to freezing. In some embodiments, the pH of the freezing medium is measured and/or adjusted prior to combination with the cells to be banked. In other embodiments, the pH of the freezing medium is measured and/or adjusted after combination with the cells to be banked. In some embodiments, the pH of the freezing medium is measured and/or adjusted more than once. In some embodiments, the pH of the freezing medium is measured and/or adjusted twice, three times, or more prior to freezing. In other embodiments, the pH of the freezing medium is measured and/or adjusted before and after combination with the cells to be banked. In some embodiments, the pH is adjusted according to the following equation: $V_{base}=C_{base}*V_p(pH_t-pH_i)$, wherein $C_{base}$ is a base-specific coefficient, $V_{base}$ is a volume of the base to add to the freezing medium, $V_p$ is the volume of the freezing medium, $pH_t$ is the target pH, and $pH_i$ is the initial pH. As used herein, the initial pH is the pH of the freezing medium containing the cells (i.e., after it is combined with the cells) but before the pH is adjusted for freezing. $C_{base}$ represents a specific coefficient that depends on the type and concentration of base chosen for pH adjustment. The $C_{base}$ coefficient can be obtained depending on the choice of base. In an exemplary embodiment, where the base is 1M sodium carbonate, the pH adjustment is performed according to Equation 1, below:

Calculation of Base Volume to add for pH Adjust $$V_{Na2CO3}=0.0085 \cdot V_p \cdot (pH_t-pH_i), \quad (1)$$

wherein $V_{Na2CO3}$ is a volume of 1M sodium carbonate to add into the freezing medium, $V_p$ is the volume of the freezing medium, $pH_t$ is the target pH, and $pH_i$ is the initial pH. The initial pH is the pH of the freezing medium containing the cells (i.e., after it is combined with the cells) but before the pH is adjusted for freezing. The target pH of the freezing medium may be a pH that is above physiological pH, such as a pH above 7.2. In some embodiments, the target pH of the freezing medium is between 7.2 and 8.3. In some embodiments, the target pH of the freezing medium is between 7.2 and 7.8. In some embodiments, the target pH of the freezing medium is at any of 7.2, 7.3, 7.4, 7.5, 7.6, 7.7, 7.8, 7.9, 8.0, 8.1, 8.2, and 8.3.

The pH of the freezing medium can be measured using methods known in the art. For example, the pH of the medium can be measured on BioProfile® 400 (Nova Biomedical) or BioProfile® FLEX (Nova Biomedical) analyzers. As used herein, all references to pH in this application, including measured pH, target pH, adjusted pH, and initial pH refer to a pH measurement taken with the sample temperature adjusted to about 37° C. (e.g., between 36° C. and 38° C. or between 35° C. and 39° C.).

III. Freezing Media

Cell freezing media provided herein may find use in methods (e.g., a method of freezing eukaryotic cells (e.g., mammalian cells, insect cells, etc.); and/or a method of improving thaw recovery of cell banks comprising eukaryotic cells (e.g., mammalian cells or insect cells)) and in compositions (e.g., a cell pool comprising a buffered solution, a cryoprotective agent, and eukaryotic cells (e.g., mammalian cells or insect cells)).

In some embodiments, a freezing medium described herein comprises a buffered solution and a cryoprotectant. In some embodiments, the buffer comprises a zwitterionic buffer. In some embodiments, the buffer includes PBS, HEPES, TES, TRIS, and TEST.

The freezing medium may comprise any cryoprotectant known in the art and described herein, such as DMSO, glycerol, ethylene glycol, non-permeating macromolecules, sugars, etc. In some embodiments, the concentration of DMSO or glycerol in the cell freezing medium is 5%-12.5% by volume (v/v) after combination with the cells to be banked. In some embodiments, the freezing medium may be provided by adding a freezing medium containing concentrated buffers and/or cryoprotectant into concentrated cells. In some embodiments, the freezing medium concentrated cryoprotective agent may contain about 20% to about 30% (v/v) DMSO or glycerol.

In some embodiments, a freezing medium may comprises additional components found in cell culture medium. In some embodiments, Ham's F10 (Sigma), Minimal Essential Medium ([MEM], Sigma), RPMI-1640 (Sigma), and Dulbecco's Modified Eagle's Medium ([DMEM], Sigma) that are suitable for culturing mammalian cells may be added into the freezing medium described herein for freezing mammalian cells. In addition, any of the media described in Ham and Wallace, Meth. Enz., 58:44 (1979), Barnes and Sato, Anal. Biochem., 102:255 (1980), Vijayasankaran et al., Biomacromolecules., 6:605:611 (2005), Patkar et al., J Biotechnology, 93:217-229 (2002), U.S. Pat. Nos. 4,767,704; 4,657,866; 4,927,762; or 4,560,655; WO 90/03430; WO 87/00195; U.S. Pat. No. Re. 30,985; or U.S. Pat. No. 5,122,469, the disclosures of all of which are incorporated herein by reference in their entirety, may be supplemented or modified as detailed herein.

As would be understood by the skilled artisan, the cell freezing medium detailed herein may comprise other components that are useful for cell culture or freezing. For example, it is understood that the media may comprise additional components such as amino acids (e.g., glutamine, arginine, or asparagine), vitamins (including but not limited to B vitamins such as any one or more of vitamin B1, vitamin B2, vitamin B3, vitamin B6, vitamin B7, vitamin B9, or vitamin B12), transition metals (including but not limited to nickel, iron (e.g., ferric iron or ferrous iron), or zinc), and other media components. Any media provided herein may also be supplemented as necessary with hormones and/or other growth factors (such as insulin, transferrin, or epidermal growth factor), ions (such as sodium, chloride, calcium, magnesium, and phosphate), buffers (such as HEPES), nucleosides (such as adenosine and thymidine), trace elements (defined as inorganic compounds usually present at final concentrations in the micromolar range), and glucose or an equivalent energy source. In some aspects, a freezing medium provided herein contains proteins derived from a plant or an animal. In some embodiments, a freezing medium provided herein is free of proteins derived from a plant or an animal. Any other necessary supplements may also be included at appropriate concentrations that would be known to those skilled in the art.

The cell freezing medium (a cell pool) as described herein may further comprise one or more cells to be banked. In an exemplary embodiment, these cells are mammalian cells, such as CHO cells. Exemplary cell types that may find use in the methods described herein include Chinese hamster ovary (CHO) cells, NS0 murine myeloma cells, PER.C6® human cells, and hybridomas. In another exemplary embodiment, these cells are insect cells, such as High Five™, S2 (Schneider 2), Sf9, and Sf21. In some embodiments, the cells are recombinant cells comprising a heterologous nucleic acid encoding a polypeptide (e.g., a therapeutic protein).As one of skill in the art would appreciate, these cells may further comprise recombinant plasmids or other useful biological compounds. In some embodiments, the cells to be banked may be useful for the production of therapeutic proteins and biological products such as antibodies, antibody fragments, enzymes, receptor fusion proteins, or fragments thereof.

IV. Eukaryotic Cells and Cell Banks

Also provided herein is a cell bank comprising a plurality of containers and each container containing a freezing medium containing an eukaryotic cell (e.g., a mammalian cell, an insect cell, etc.) comprising a nucleic acid (e.g., a heterologous nucleic acid) encoding a polypeptide, wherein the medium has a pH of about 6.7 to about 8.5 prior to freezing the cell. The cell bank may be a Prebank, a master cell bank (MCB), or a working cell bank (WCB). A Prebank may comprise frozen (e.g., stored in liquid nitrogen freezer) containers (e.g., ampoules) containing cells producing a specific polypeptide from which a MCB is prepared. A MCB may comprise frozen (e.g., stored in liquid nitrogen freezer) containers (e.g., ampoules) containing a cell culture derived from the subculture of the Prebank and from which all subsequence cells for production are derived. MCBs are produced and stored in accordance with cGMPs and may be used for the production of polypeptide product. A WCB may comprise frozen (e.g., stored in liquid nitrogen freezer) containers (e.g., ampoules) containing a cell culture derived from the subculture of the MCB. WCBs are produced and stored in accordance with cGMPs and may be used for the production of polypeptide product. In some embodiments, the containers are ampoules.

Eukaryotic cells (e.g., mammalian cells, insect cells, etc.) that can be frozen in a freezing medium and stored as described herein may include any eukaryotic cells that can be cultured and/or are useful for producing a polypeptide. In some embodiments, the cell is a mammalian cell, such as a Chinese Hamster Ovary (CHO) cell. CHO cells may include, but are not limited to, DHFR⁻ CHO cells (Urlaub et al., Proc. Natl. Acad. Sci. USA 77:4216 (1980)), e.g., ATCC® CRL-9096™; and CHO-K1 (ATCC® CRL-61™).

Other examples of mammalian cells include, without limitation, monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). Other useful mammalian host cell lines include myeloma cell lines such as NS0 and Sp2/0. For a review of certain mammalian host cell lines suitable for antibody production, see, e.g., Yazaki and Wu, *Methods in Molecular Biology, Vol.* 248 (B. K. C. Lo, ed., Humana Press, Totowa, N.J., 2003), pp. 255-268.

In some embodiments, the cell is an insect cell line, such as High Five™, S2 (Schneider 2), Sf9, and Sf21.

In some embodiments, the cells described herein (e.g., mammalian cell, or insect cells) comprise a nucleic acid (e.g., a heterologous nucleic acid) encoding a polypeptide and the cells are useful for producing the polypeptide. In some embodiments, the nucleic acid is introduced into the cells. Any methods known in the art for introducing a nucleic acid into a cell may be used. For example, the cells may be transformed with vectors (e.g., an expression vector) comprising one or more nucleic acids encoding the polypeptide. In some embodiments, the cell is a stable cell line. In some embodiments, the polypeptide is selected from the group consisting of an antibody, an antibody fragment, an enzyme, and a receptor fusion protein.

Examples of polypeptides include mammalian proteins, such as, e.g., renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-b; platelet-derived growth factor (PDGF); fibroblast growth factor such as aFGF and bFGF; epidermal growth factor (EGF); transforming growth factor (TGF) such as TGF-alpha and TGF-beta, including TGF-β31, TGF-β2, TGF-β3, TGF-β4, or TGF-β5; insulin-like growth factor-I and -II (IGF-I and IGF-IT); des(1-3)-IGF-I (brain IGF-I), insulin-like growth factor binding proteins (IGFBPs); CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as CA125 (ovarian cancer antigen) or HER2, HER3 or HER4 receptor; immunoadhesins; and fragments and/or variants of any of the above-listed proteins as well as antibodies, including antibody fragments, binding to a protein, including, for example, any of the above-listed proteins.

In some embodiments, the cells described herein (e.g., mammalian cells, or insect cells) comprises a nucleic acid encoding an antibody. In some embodiments, the antibody is a monoclonal antibody. The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by a variety of techniques, including, for example, the hybridoma method (e.g., Kohler and Milstein, *Nature,* 256:495-97 (1975); Hongo et al., *Hybridoma,* 14 (3): 253-260 (1995), Harlow et al., *Antibodies: A Laboratory Manual,* (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352: 624-628 (1991); Marks et al., *J. Mol. Biol.* 222: 581-597 (1992); Sidhu et al., *J. Mol. Biol.* 338(2): 299-310 (2004); Lee el al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, Nature Biotechnol. 14: 826 (1996); and Lonberg and Huszar, Intern. Rev. Immunol. 13: 65-93 (1995). In some embodiments, the antibody is a humanized antibody, a chimeric antibody, a human antibody, a library-derived antibody, or a multispecific antibody. In some embodiments, the antibody is an antigen-binding fragment thereof. Examples of antigen-binding fragment include Fab, Fab', F(ab')$_2$, and Fv fragments; diabodies; linear antibodies; single-chain antibody molecules; and multispecific antibodies formed from antibody fragments. The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known. "Fv" is the minimum antibody fragment which contains a complete antigen-binding site. "Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthïn, in *The Pharmacology of Monoclonal Antibodies*, vol. 113, Rosenburg and Moore eds., (Springer-Verlag, New York, 1994), pp. 269-315. Many of the methods for purifying an antibody described above may be suitably adapted for purifying an antigen-binding antibody fragment.

In some embodiments, the antibodies encoded by the nucleic acid in the cells (e.g., mammalian cells, or insect cells) including therapeutic and diagnostic antibodies. Antibodies within the scope of the present invention include, but are not limited to: anti-HER2 antibodies including Trastuzumab (HERCEPTIN®) (Carter et al., Proc. Natl. Acad. Sci, USA, 89:4285-4289 (1992), U.S. Pat. No. 5,725, 856); anti-CD20 antibodies such as chimeric anti-CD20 "C2B8" as in U.S. Pat. No. 5,736,137 (RITUXAN®), a chimeric or humanized variant of the 2H7 antibody as in U.S. Pat. No. 5,721,108B1, or Tositumomab (BEXXAR®); anti-IL-8 (St John et al., Chest, 103:932 (1993), and International Publication No. WO 95123865); anti-VEGF antibodies including humanized and/or affinity matured anti-VEGF antibodies such as the humanized anti-VEGF antibody huA4.6.1 AVASTINO (Kim et al., Growth Factors, 7:53-64 (1992), International Publication No. WO 96/30046, and WO 98/45331, published Oct. 15, 1998); anti-PSCA antibodies (WO01/40309); anti-CD40 antibodies, including S2C6 and humanized variants thereof (WO00/75348); anti-CD11a (U.S. Pat. No. 5,622,700, WO 98/23761, Steppe et al., Transplant Intl. 4:3-7 (1991), and Hourmant et al., Transplantation 58:377-380 (1994)); anti-IgE (Presta et al., J. Immunol. 151:2623-2632 (1993), and International Publication No. WO 95/19181); anti-CD18 (U.S. Pat. No. 5,622,700, issued Apr. 22, 1997, or as in WO 97/26912, published Jul. 31, 1997); anti-IgE (including E25, E26 and E27; U.S. Pat. No. 5,714,338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714,338); anti-Apo-2 receptor antibody (WO 98/51793 published Nov. 19, 1998); anti-TNF-α antibodies including cA2 (REMICADE®), CDP571 and MAK-195 (See, U.S. Pat. No. 5,672,347 issued Sep. 30, 1997, Lorenz et al., J. Immunol. 156(4):1646-1653 (1996), and Dhainaut et al., Crit. Care Med. 23(9):1461-1469 (1995)); anti-Tissue Factor (TF) (European Patent No. 0 420 937 B1 granted Nov. 9, 1994); anti-human $\alpha_4\beta_7$ integrin (WO 98/06248 published Feb. 19, 1998); anti-EGFR (chimerized or humanized 225 antibody as in WO 96/40210 published Dec. 19, 1996); anti-CD3 antibodies such as OKT3 (U.S. Pat. No. 4,515,893 issued May 7, 1985); anti-CD25 or anti-tac antibodies such as CHI-621 (SIMULECT®) and (ZENAPAX®) (See U.S. Pat. No. 5,693,762 issued Dec. 2, 1997); anti-CD4 antibodies such as the cM-7412 antibody (Choy et al., Arthritis Rheum 39(1):52-56 (1996)); anti-CD52 antibodies such as CAMPATH-1H (Riechmann et al., Nature 332:323-337 (1988)); anti-Fc receptor antibodies such as the M22 antibody directed against Fc.gamma.R1 as in Graziano et al., J. Immunol. 155(10):4996-5002 (1995); anti-carcinoembryonic antigen (CEA) antibodies such as hMN-14 (Sharkey et al., Cancer Res. 55(23 Suppl): 5935s-5945s (1995); antibodies directed against breast epithelial cells including huBrE-3, hu-Mc 3 and CHL6 (Ceriani et al., Cancer Res. 55(23): 5852s-5856s (1995); and Richman et al., Cancer Res. 55(23 Supp): 5916s-5920s (1995)); antibodies that bind to colon carcinoma cells such as C242 (Litton et al., Eur J. Immunol. 26(1): 1-9 (1996)); anti-CD38 antibodies, e.g. AT 13/5 (Ellis et al., J. Immunol. 155(2):925-937 (1995)); anti-CD33 antibodies such as Hu M195 (Jurcic et al., Cancer Res 55(23 Suppl):5908s-5910s (1995) and CMA-676 or CDP771; anti-CD22 antibodies such as LL2 or LymphoCide (Juweid et al., Cancer Res 55(23 Suppl):5899s-5907s (1995)); anti-EpCAM antibodies such as 17-1A (PANOREX®); anti-GpIIb/IIIa antibodies such as abciximab or c7E3 Fab (REOPRO®); anti-RSV antibodies such as MEDI-493 (SYNAGIS®); anti-CMV antibodies such as PROTOVIR®; anti-HIV antibodies such as PRO542; anti-hepatitis antibodies such as the anti-Hep B antibody OSTAVIR®; anti-CA 125 antibody OvaRex; anti-idiotypic GD3 epitope antibody BEC2; anti-αvβ3 antibody VITAXIN®.; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1). The preferred target antigens for the antibody herein are: HER2 receptor, VEGF, IgE, CD20, CD11a, and CD40.

The following Examples are provided to illustrate but not to limit the invention.

EXAMPLES

Example 1

Effect of Pool pH, Hold Temperature and Hold Time on Thawed Cell Viability

Base Addition Method to Control Banking pH (Small Scale Study #1)

A study was executed to gauge the feasibility of performing a simple pH adjustment from worst case and typical pool conditions (targeted initial pH of 6.2 and 6.7 respectively) to enhance thaw recovery. Several pH adjustment targets were studied to determine optimal banking pH. The pH was measured using the on BioProfile® 400 (Nova Biomedical) instrument with the temperature set to 37° C. Similarly, pH calculations using Equation 1 are based upon a sample temperature of 37° C.

Cells were pelleted via centrifugation. Cell pools were generated for each test condition by resuspending cells to $100\times10^6$ cells/mL in spent media. The cell pools were agitated at 37° C. with or without gas permeable membranes for $CO_2/O_2$ exchange to drive pH to initial pH conditions (either 6.2 or 6.7). Upon reaching initial pH targets, pools were quickly chilled to <10° C. and 20% (v/v) DMSO freeze media was added (1:3 parts cell culture fluid). pH adjustments were performed using Equation 1 to calculate required volumes of 1M sodium carbonate addition to target pH of 6.9, 7.1, and 7.3 and a final offline pH measurement was taken to confirm an appropriate increase in pH prior to mock bank generation (actual banking pH was 6.9, 7.1/7.2 and 7.5).

Figure 2A:
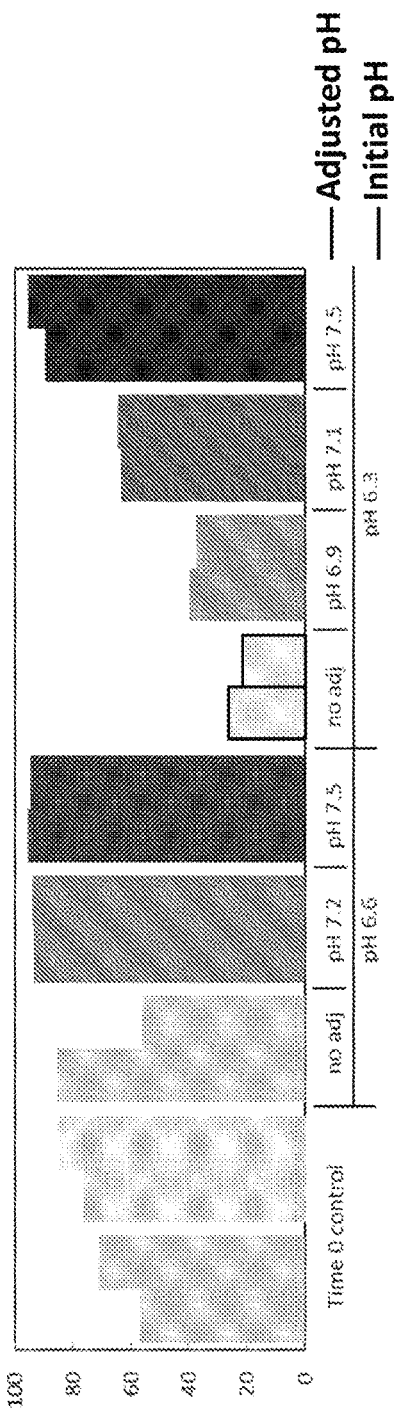
FIGS. 2A-2B show thaw passage day 1 viability (FIG. 2A) and day 4 growth (PCV) (FIG. 2B) results for cell banks generated from pH adjusted pools at initial pH of 6.6 or 6.3.
Figure 2B:
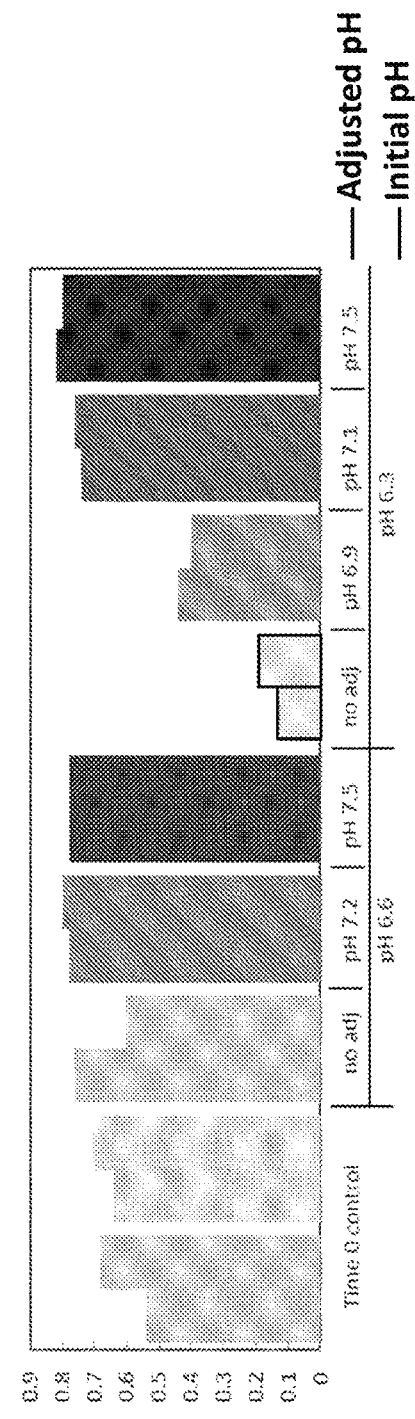
Figures 4A, 4B:
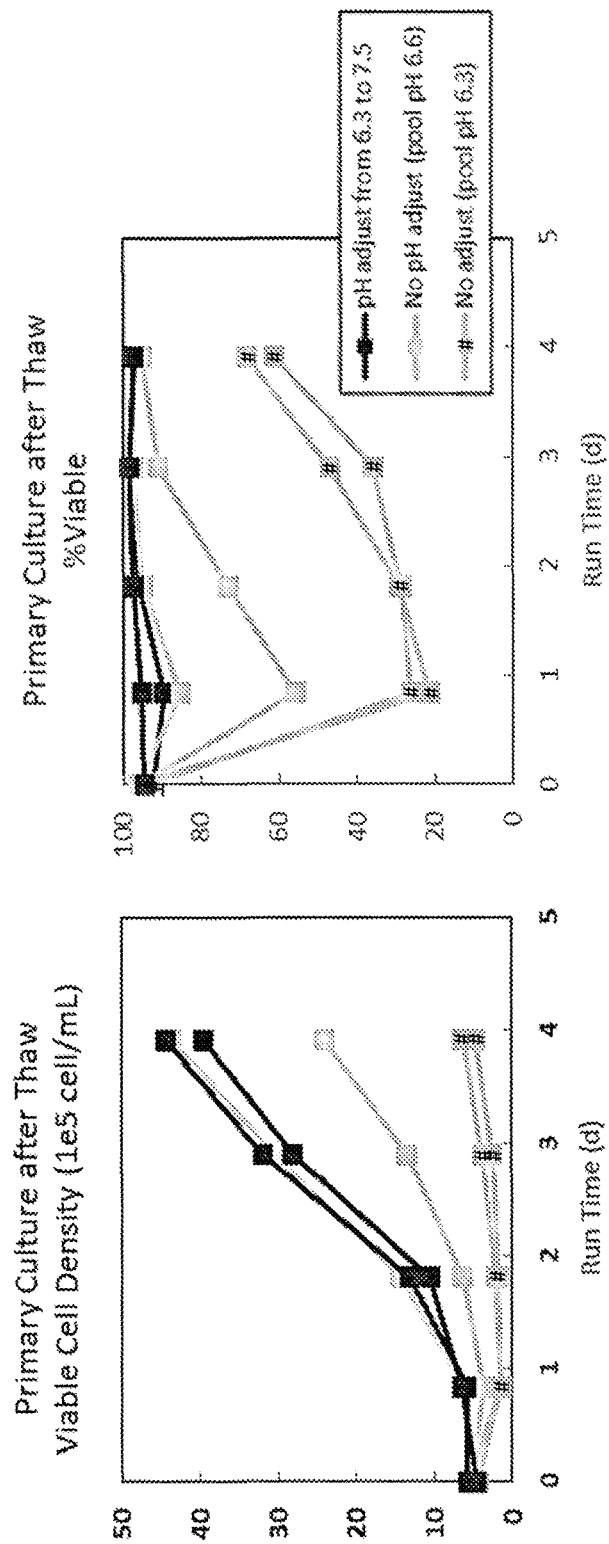
FIGS. 4A-4B show thaw passage viable cell density (VCD) or viable cell count (VCC) (FIG. 4A) and viability (%) (FIG. 4B) trends, which demonstrate the effect of adjusting pH to 7.5 from an initial pool pH of 6.3 vs. no pH adjustment.

Thaw results showed a dramatic improvement in day 1 viability of up to 68% (from 24% to 92% for the adjustment from pH 6.2 to 7.5) (FIG. 2A), and improvement in day 4 PCV of up to 0.64% (from 0.17% to 0.81% for the adjustment from pH 6.2 to 7.5) (FIG. 2B).

Calculation of Base Volume to add for pH Adjust $$V_{Na2CO3}=0.0095 \cdot V_p \cdot (pH_t-pH_i),\quad(1)$$

where $V_{Na2CO3}$=Volume of 1M Sodium Carbonate to add, $V_p$=Volume of Pool, $pH_t$=Target pH, $pH_i$=Initial pH, Base Addition Method to Control Banking pH (Additional Small Scale pH Studies)

Following similar procedures described above, several studies were executed to study the effect of pH adjustment on additional cell lines.

A total of nine CHO cell lines covering various cell types (DP12, CHO-K1) were selected. In the days prior to banking, cells were maintained according to standard protocols. Cells were pelleted via centrifugation and mock pools of approximately 60-90 mL were generated for each test condition by re-suspending in spent media to 28% packed cell volume (PCV). The pools were agitated at 37° C. with or without gas permeable membranes for $CO_2/O_2$ exchange to drive pH to initial pH conditions (either 6.2 or 6.7). These two initial pH set points were chosen to simulate potential worst case and typical conditions experienced during and after hollow-fiber filter concentration. Upon reaching initial pH targets, pools were quickly chilled to <10° C. and 20% (v/v) DMSO freeze media was added (1:3 parts cell culture fluid) to reach a final PCV of 21%. pH adjustments were performed after using Equation 1 to calculate the required volume of 1M sodium carbonate addition for adjustment to pH 7.0, 7.3, 7.6, or 8.0. A final offline pH measurement was taken to confirm an appropriate increase in pH prior to cell bank generation.

All cases were thawed in duplicate with one ampoule thawing into each vessel. Results demonstrated that all cell types previously exposed to lower pH could recover when adjusted to pH values above 7.3 prior to banking. Each cell line demonstrated different sensitivity to banking pH. Adjustment to a pH of approximately 7.5 resulted in day 1 thaw viabilities above 80% in most cases (FIGS. 3A-3F and FIGS. 4A-4B). Growth rates after thaw were only impacted at the lower end of the pH range tested. Interestingly, the upper end of the pH range tested (near 8.0-8.2) did not negatively impact thaw recovery despite being significantly greater than normal physiological pH.

Figure 6A:
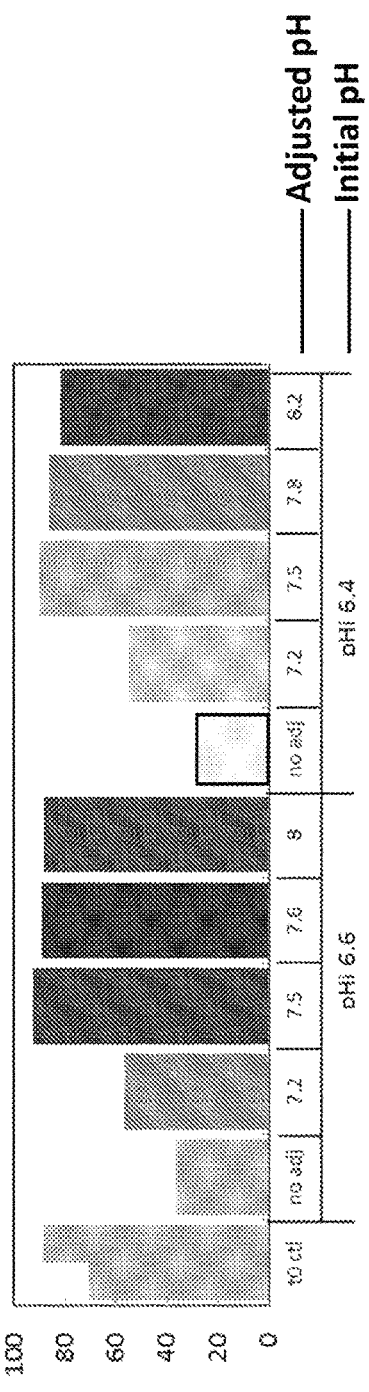
FIGS. 6A-6B show thaw passage overall growth rate by PCV results for cell banks generated from pH adjusted pools at an initial pH of 6.4 (target 6.2) or 6.6 (target 6.7) at t0 (FIG. 6A) and t2 (2 hours) (FIG. 6B).
Figure 6B:
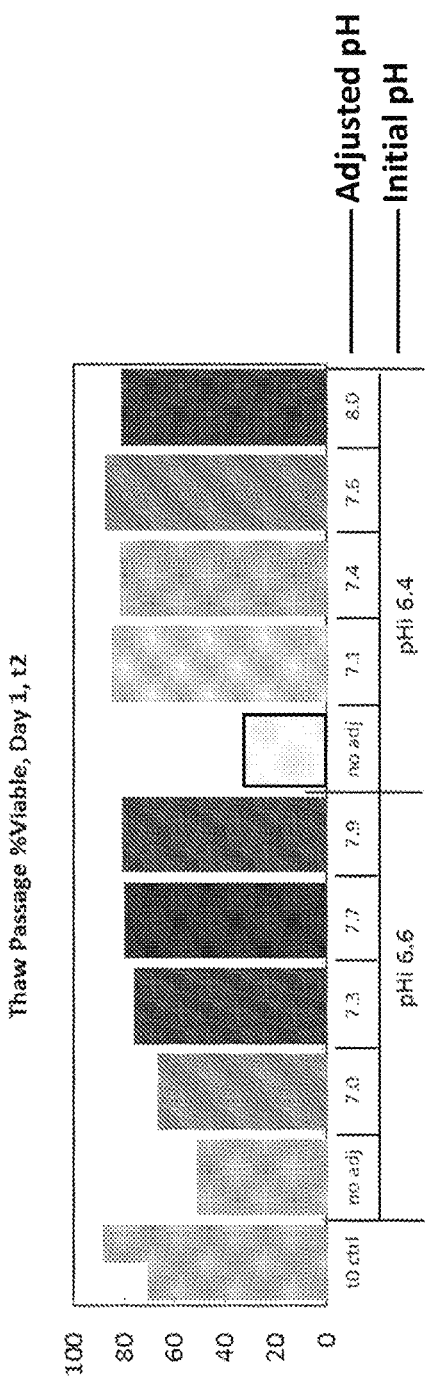

The studies (testing the CHO-K1 cell types) were expanded to capture more information about long term exposure to high pH. These studies tested mock banks frozen immediately after (t0) the pH adjustment (similar to all previous small scale test cases) and at a second time point two hours later (t2). During the 2 hour hold, the miniature pools (approximately 10 mL per case) were held in Falcon® tubes submerged in wet ice. There was a slight pH drift over the hold step that resulted in a change of up to 0.2 pH units. Results from these studies indicated that a two hour exposure to the pH ranges tested in this study had no impact (an example is shown in FIGS. 6A-6B).

Methods to Chill Cell Culture Fluid During Harvest

A "slow pump harvest" process in combination with a cooling heat exchanger was adopted to introduce chilling capability into the traditional cell banking process. Specifically, the "slow pump harvest" process required reducing the typical harvest flow rate from approximately 4 L/min to 600 mL/min to match harvest rates recorded for traditional cell banking production runs. A cooling heat exchanger line, 15' length of size 15 platinum-cured silicone tubing fully submerged in wet ice, was inserted into the harvest flowpath. Temperature trends obtained during a mock run with water demonstrated that the "chilled harvest process" was capable of reducing culture temperatures to approximately 12° C. within the first 30 minutes prior to hollow-fiber filter concentration. Based on data at 10° C., this chilling capability would likely suspend cell metabolism and prevent a low pH drift.

Process Confirmation Study Results

Cell Banking Process. Cell banks were produced by first accumulating suspension-adapted CHO cells in a batch/perfusion cell culture process and then harvesting cells for banking. The initial source of cells was from an MCB (for WCB generation). The process involved three stages: cell accumulation, harvest and cell concentration, and cell banking. The purpose of the cell accumulation step was to generate the number of cells required for production of a full-size MCB or WCB (420×1 mL or 10 mL ampoules respectively) in a single batch. Cells were cultured in selective seed train media during initial scale-up and during a rocking bioreactor process. A harvest process step served to concentrate the final cell culture fluid via a hollow fiber filter (HFF) to cell densities required for banking. A subsequent pooling and filling process served to prepare cell bank ampoules for long-term storage. The pooling process was held on wet ice such that a certain temperature range (about 5-10° C.) was maintained. The process flow for the process is shown in FIG. 1.

Harvest and cell concentration processes were executed using a hollow-fiber filter cartridge. Offline pH trends showed that the "chilled harvest process" was effective in reducing the pH drop during cell concentration by approximately 0.35 pH units (from ~6.30 to 6.66 for the original and "chilled" processes respectively). After pH adjustment, chilled cell banks were created at early (0 min) and late (120 min) timepoints to check for transient impact of cell pool hold pH.

Resulting cell banks were assessed for performance in primary culture. Cell bank ampoules were thawed into shake flasks rather than bioreactors using a serial 1:250 dilution (1:10, then 1:25). Thaw results successfully demonstrated that the current process (chilled harvest and pH adjustment) was capable in delivering banks with acceptable thaw performance. Whereas, cell bank generated from the original process experienced a decline in viability, these new cell banks were consistent and ranged from 79.1-85.3% in day 1 viability (approximately 65% improvement). No adverse impact was observed as cells were held at elevated pH over time.

Figure 5:
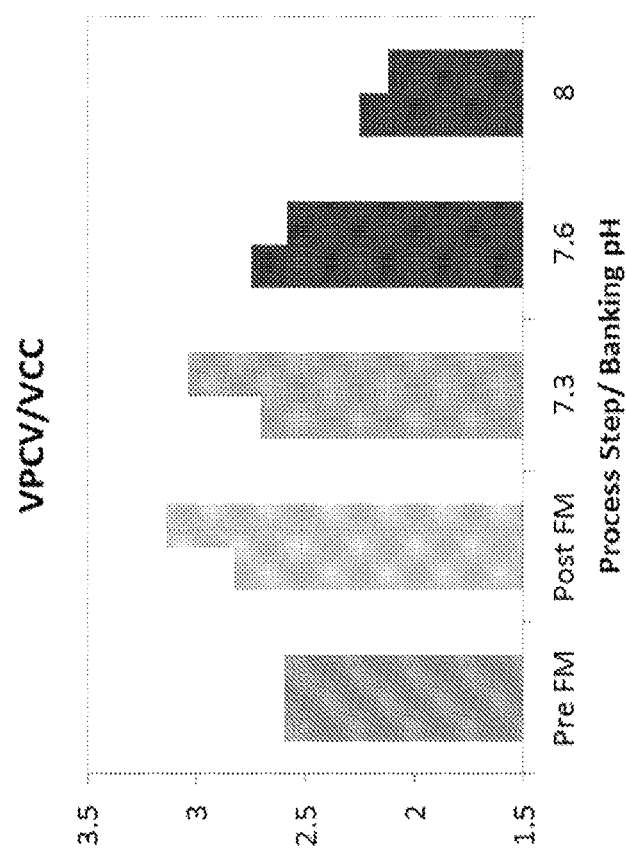
FIG. 5 shows the ratio of viable packed cell volume (VPCV) to viable cell count (VCC), which is an indirect means of estimating cell size, during the pooling process. The data show the effect of freeze media (FM) addition and pH adjustment to pH 7.3, 7.6 or 8.0 on cell size. A larger ratio indicates a larger cell size.

Analysis showed cells from pools adjusted to higher pHs were smaller in size (FIG. 5). This observed shift in size could indicate that higher pH causes cell dehydration (possibly from increased osmotic pressure or enhanced cell membrane elasticity allowing cell shrinkage or both).

Conclusions

Banking pH was determined to be most critical to post thaw performance, impacting day 1 thaw viabilities by up to 65%. As such, process enhancements made to the harvest and banking procedure were designed to mitigate cell exposure to low pH and to improve control over banking pH. Ultimately, two enhancements were introduced to the process including: 1) chilling cell culture fluid during harvest with silicone tubing heat exchanger; and 2) using a pH adjustment step to increase banking pH to 7.5.

What is claimed is:

1. A cell bank comprising a plurality of containers, each container containing (a) a freezing medium comprising a buffered solution and a cryoprotective agent, and (b) Chinese hamster ovary (CHO) cells comprising a nucleic acid encoding a polypeptide, wherein the freezing medium has a pH of 7.7 to 8.3 prior to freezing the CHO cells.

2. The cell bank of claim 1, wherein the containers are ampoules.

3. The cell bank of claim 1, wherein the polypeptide is a therapeutic protein.

4. The cell bank of claim 3, wherein the therapeutic protein is selected from the group consisting of an antibody, an antibody fragment, an enzyme, and a receptor fusion protein.

5. The cell bank of claim 1, wherein each container comprises a cell pool.

6. The cell bank of claim 1, wherein the cryoprotective agent is selected from the group consisting of DMSO, glycerol, propanediol, ethylene glycol, a macromolecule, a sugar, or a combination thereof.

7. The cell bank of claim 1, wherein the cryoprotective agent is DMSO or glycerol at a concentration of about 5% to about 10% by volume.

8. The cell bank of claim 1, wherein the CHO cells are at a density of about 8% to about 28% packed cell volume (PCV) prior to freezing.

\* \* \* \* \*